United States Patent
Brown et al.

(10) Patent No.: US 6,626,950 B2
(45) Date of Patent: Sep. 30, 2003

(54) COMPOSITE SCAFFOLD WITH POST ANCHOR FOR THE REPAIR AND REGENERATION OF TISSUE

(75) Inventors: Kelly R. Brown, Hillsborough, NJ (US); Mark C. Zimmerman, East Brunswick, NJ (US); Yufu Li, Bridgewater, NJ (US)

(73) Assignee: Ethicon, Inc., Somerville, NJ (US)

( * ) Notice: Subject to any disclaimer, the term of this patent is extended or adjusted under 35 U.S.C. 154(b) by 37 days.

(21) Appl. No.: 09/893,813

(22) Filed: Jun. 28, 2001

(65) Prior Publication Data

US 2003/0004578 A1 Jan. 2, 2003

(51) Int. Cl.$^7$ .................................................. A61F 2/36
(52) U.S. Cl. ................. 623/23.72; 623/23.75; 623/23.76
(58) Field of Search ............................. 623/13.14, 13.15, 623/20.17, 23.56, 23.58, 23.72, 23.73, 23.74, 23.75, 23.76; 424/427, 425, 426; 435/41

(56) References Cited

U.S. PATENT DOCUMENTS

| | | |
|---|---|---|
| 3,929,971 A | 12/1975 | Roy |
| 4,045,418 A | 8/1977 | Sinclair |
| 4,057,537 A | 11/1977 | Sinclair |
| 4,105,034 A | 8/1978 | Shalaby et al. |
| 4,130,639 A | 12/1978 | Shalaby et al. |
| 4,140,678 A | 2/1979 | Shalaby et al. |
| 4,141,087 A | 2/1979 | Shalaby et al. |
| 4,186,448 A | 2/1980 | Brekke |
| 4,205,399 A | 6/1980 | Shalaby et al. |
| 4,208,511 A | 6/1980 | Shalaby et al. |
| 4,479,271 A | * 10/1984 | Bolesky et al. |
| 4,861,733 A | 8/1989 | White |
| 5,067,964 A | 11/1991 | Richmond et al. |
| 5,084,051 A | 1/1992 | Tormala et al. |

(List continued on next page.)

FOREIGN PATENT DOCUMENTS

| | | |
|---|---|---|
| DE | 199 33 382 | 7/1999 |
| EP | 0274898 | 7/1988 |
| EP | 0278583 | 8/1988 |
| EP | 0464163 | 1/1992 |
| EP | 1027897 | 8/2000 |
| EP | 1264607 | 5/2002 |

(List continued on next page.)

OTHER PUBLICATIONS

A.F. Tencer, et al., "Compressive Properties Of Polymer Coated Synthetic Hydroxyapatite For Bone Grafting", Journal of Biomedical Materials Research, vol. 19, John Wiley & Sons, Inc., (1985), pp. 957–969.

(List continued on next page.)

Primary Examiner—Nicholas D. Lucchesi
Assistant Examiner—Lalita M. Hamilton

(57) ABSTRACT

A prosthetic implant having a tissue scaffold and a fixation device with a scaffold support and an anchoring post. The anchoring post extends from a surface of the scaffold support at a selected angle with the scaffold support embedded within the scaffold. The scaffold has a porous ceramic phase and a porous polymer phase. The polymer is foamed while in solution that is infused in the pores of the ceramic to create a interphase junction of interlocked porous materials and embedding the scaffold support portion of the fixation device. The preferred method for foaming is by lyophilization. The scaffold may be infused or coated with a variety of bioactive materials to induce ingrowth or to release a medicament. The mutilayered porous scaffold can mimic the morphology of an injured tissue junction with a gradient morphology and cell composition.

24 Claims, 3 Drawing Sheets

U.S. PATENT DOCUMENTS

| | | | |
|---|---|---|---|
| 5,108,755 A | * 4/1992 | Daniels et al. |
| 5,133,755 A | 7/1992 | Brekke |
| 5,306,311 A | * 4/1994 | Stone et al. |
| 5,314,478 A | 5/1994 | Oka et al. |
| 5,314,989 A | 5/1994 | Kennedy et al. |
| 5,403,347 A | 4/1995 | Roby et al. |
| 5,431,679 A | 7/1995 | Bennett et al. |
| 5,458,643 A | 10/1995 | Oka et al. |
| 5,464,929 A | 11/1995 | Bezwada et al. |
| 5,468,253 A | 11/1995 | Bezwada et al. |
| 5,486,359 A | 1/1996 | Caplan et al. |
| 5,502,159 A | 3/1996 | Liu et al. |
| 5,514,378 A | 5/1996 | Mikos et al. |
| 5,522,895 A | 6/1996 | Mikos |
| 5,595,751 A | 1/1997 | Bezwada et al. |
| 5,597,579 A | 1/1997 | Bezwada et al. |
| 5,607,474 A | 3/1997 | Athanasiou et al. |
| 5,607,687 A | 3/1997 | Bezwada et al. |
| 5,618,552 A | 4/1997 | Bezwada et al. |
| 5,620,698 A | 4/1997 | Bezwada et al. |
| 5,624,463 A | 4/1997 | Stone et al. |
| 5,632,745 A | 5/1997 | Schwartz |
| 5,645,850 A | 7/1997 | Bezwada et al. |
| 5,648,088 A | 7/1997 | Bezwada et al. |
| 5,677,355 A | 10/1997 | Shalaby et al. |
| 5,686,091 A | 11/1997 | Leong et al. |
| 5,698,213 A | 12/1997 | Jamiolkowski et al. |
| 5,700,583 A | 12/1997 | Jamiolkowski et al. |
| 5,711,960 A | 1/1998 | Shikinami |
| 5,713,374 A | 2/1998 | Pachence et al. |
| 5,716,413 A | 2/1998 | Walter et al. |
| 5,723,508 A | 3/1998 | Healy et al. |
| 5,749,874 A | 5/1998 | Schwartz |
| 5,755,792 A | 5/1998 | Brekke |
| 5,769,899 A | 6/1998 | Schwartz et al. |
| 5,770,193 A | 6/1998 | Vacanti et al. |
| 5,770,417 A | 6/1998 | Vacanti et al. |
| 5,859,150 A | 1/1999 | Jamiolkowski et al. |
| 6,103,255 A | 8/2000 | Levene et al. |
| 6,146,426 A | * 11/2000 | Doyle |
| 6,251,143 B1 | 6/2001 | Schwartz et al. |

FOREIGN PATENT DOCUMENTS

| | | |
|---|---|---|
| WO | 9916478 | 4/1999 |
| WO | 9916479 | 4/1999 |
| WO | 0020354 | 4/2000 |
| WO | 0143667 | 6/2001 |

OTHER PUBLICATIONS

Ainslie T. Young, "Microcellular Foams via Phase Separation" J. Vac. Sci. Technol. A 4 (3), American Vacuum Society (May/Jun. 1986), pp. 1128–1133.

Daniel Cohn, et al., "Biodegradable PEO/PLA Block Copolymers" Journal of Biomedical Materials Research, vol. 22, John Wiley & Sons, Inc., (1988), pp. 993–1009.

Allcock, "Polyphosphazenes", Encyclopedia of Polymer Science and Engineering, vol. 13, John Wiley & Sons, Inc., New York (1988), pp. 31–41.

D. Cohn, "New Tailor–Made Biodegradable Polymeric Biomaterials" Polymer Preprints, vol. 30, No. 1, Division of Polymer Chemistry, Inc., Dallas, Texas, (Apr. 1989), p. 498.

Shigenobu Matsuda, "Thermodynamics of Formation of Porous Polymeric Membrane from Solutions", Polymer Journal, vol. 23, No. 5, (1991), pp. 435–444.

Jorge Heller, "Poly(ortho esters)", Handbook Of Biodegradable Polymers, Harwood Academic Publishers, Netherlands, (1997), pp. 99–118.

J. Vandorpe, et al., "Biodegradable Polyphosphazenes For Biomedical Applications", Handbook Of Biodegradable Polymers, Harwood Academic Publishers, Netherlands, (1997), pp. 161–182.

John Kemnitzer, et al., "Degradable Polymers Derived From the Amino Acid L–Tyrosine", Handbook Of Biodegradable Polymers, Harwood Academic Publishers, Netherlands, (1997), pp. 251–272.

B. Kreklau, et al., "Tissue Engineering of Biphasic Joint Cartilage Transplants", Biomaterials 20, Elsevier Science Ltd., (1999), pp. 1743–1749.

Gabriele G. Niederauer, et al., "Evaluation of Multiphase Implants for Repair of Focal Osteochondral Defects in Goats", Biomaterials 21, Elsevier Science Ltd., (2000), pp. 2561–2574.

D. Schaefer, et al., "In Vitro Generation of Osteochondral Composites", Biomaterials 20, Elsevier Science Ltd., (2000), pp. 2599–2606.

Vicki Rosen, Ph.D, et al., "Chapter 1—Introduction and Goal", The Cellular and Molecular Basis of Bone Formation and Repair, R.G. Landes Company, Austin, Texas, (1995), pp. 1–41.

* cited by examiner

COMPOSITE SCAFFOLD WITH POST ANCHOR FOR THE REPAIR AND REGENERATION OF TISSUE

FIELD OF THE INVENTION

The present invention relates generally to the field of tissue repair and more particularly to composite scaffold implants and scaffold fixation devices with post-type anchors received in a hole formed in underlying tissue.

BACKGROUND OF THE INVENTION

Porous ceramic materials such as hydroxyapatite, soluble glasses and ceramic forms have been used as scaffolds for the ingrowth of tissue due to compositional and morphological biocompatability. For example, the porosity of such materials promotes cell infiltration. A variety of methods are used to prepare porous ceramic scaffolds (prostheses), such as hydrothermally treating animal bone or coral, burning off polymer beads mixed into a ceramic body, vapor deposition on foam, infiltration of polymer foam with a ceramic slip and foaming a ceramic slip.

One limitation exhibited by porous ceramic materials is their inherent brittleness. Attempts to address this limitation have included back-filling a ceramic foam with monomer solutions of PMMA or PLA, draining excess solution from the ceramic foam then polymerizing through curing and/or drying in order to impart some toughness to the ceramic foam. Others have proposed laminating solid or porous polymeric layers to a ceramic foam structure.

Independent from proposed uses in combination with ceramics, polymeric foams have utility in the repair and regeneration of tissue. For example, amorphous, polymeric foam has been used to fill voids in bone. Various methods have been explored for preparing the polymer foams, using, e.g., leachables; vacuum foaming techniques; precipitated polymer gel masses; and polymer melts with fugitive compounds that sublime at temperatures greater than room temperature. The formation of biocompatible absorbable foams by lyophilization is discussed in a copending patent application entitled "Porous Tissue Scaffoldings for the Repair and Regeneration of Tissue", assigned to Ethicon, Inc., docket number 09/345096, filed Jun. 30, 1999, hereby incorporated by reference.

Hinsch et al. (EP0274898) describes a porous open cell foam of polyhydroxy acids for the in growth of blood vessels and cells. The foam can be reinforced with fibers, yarns, braids, knitted fabrics, scrims and the like.

Athanasiou et al. (U.S. Pat. No. 5,607,474) have proposed using a two-layer polymeric foam device for repairing osteochondral defects at a location where two dissimilar types of tissue are present. The two polymeric layers are prepared separately, and joined together at a subsequent step. Each of the layers is designed to have stiffness and compressibility values that correspond respectively to cartilage and bone tissue, mimicking the cartilage/bone interface. However, the Athanasiou device exhibits an abrupt change in properties from one layer to the next, whereas the juncture of cartilage and bone displays a gradual transition, with cartilage cells gradually changing cell morphology and orientation depending on the location relative to the underlying bone structure. Further, collagen fiber orientation within the matrix also changes relative to its location in the structure.

H. Levene et al., U.S. Pat. No. 6,103,255 describes a process used for making a scaffold having a substantially continuous polymer phase with a distribution of large and small pore sizes, with the small pores contained in the walls of the large pores.

In a study done by G. Niederauer et al. and reported in *Biomaterials* 21 (2000) 2561, scaffolds for articular cartilage repair were prepared from layers of polylactic/polyglycolic acid (PLG) and polylactic/polyglycolic acid reinforced with fibers of the same material, bioglass or calcium sulfate. The PLG layer was made porous in all cases by expanding a precipitated gel mass of polymer under vacuum at elevated temperatures. The reinforced layers were made porous in a similar fashion after incorporating the reinforcement in the polymer solution and prior to precipitation of the polymeric gel mass. Once the two layers were fabricated, they were adjoined using a small amount of solvent to glue the two layers together.

The use of a porous polymer for the purpose of engineering cartilage is described in the patent by T. Mahood et al. (EP1027897A1) which discloses a multi-layer polymer scaffold in which the layers are attached by successive dip coating or by the attachment of the two layers to a third. The third layer is described as a barrier to cell diffusion, thus confining chondrocytes to the polymer layer and osteoblasts to the ceramic layer.

Kreklau et al. in *Biomaterials* 20 (1999) 1743 have evaluated a fibrous polymeric fleece attached to a porous ceramic material, for the purpose of culturing chondrocytes in the polymeric scaffold while simultaneously providing a bone formation inducing absorbable material to simulate articular cartilage. In this study, a fibrin-cell-solution was used to affix the ceramic and polymeric layers by way of encapsulation with the intent that the phases would interact in vitro in order to create a mechanically stressable junction. The authors discuss the possibility of providing the surfaces of the layers with teeth to increase shear strength. However, there is no mechanism by which the two different layers are interlocked to resist delaminating forces in directions perpendicular to the laminate function and there is an abrupt transition between the two layers.

In addition to the limitations of the prior art relative to the composition and morphology of tissue scaffolds, the fixation of the scaffold at the site of injury remains challenging. Various fixation methods have been explored, including press-fitting the scaffold into the defect (which may result in slippage or destruction of the implanted scaffold) or suturing the scaffold to the periosteal flaps. The latter approach is not always ideal because the geometry of the scaffold may not match that of the periosteal flaps or the flaps may have been destroyed or cannot be located.

It would therefore be advantageous to overcome the above mentioned limitations with a scaffold that provides secure attachment to a defect site.

SUMMARY OF THE INVENTION

The limitations of the prior art are solved by the present invention which includes a prosthetic implant having a tissue scaffold and a fixation device with a scaffold support and an anchoring post. The anchoring post extends from a surface of the scaffold support at a selected angle with the scaffold support embedded within the scaffold.

DETAILED DESCRIPTION OF THE INVENTION

Figure 2:
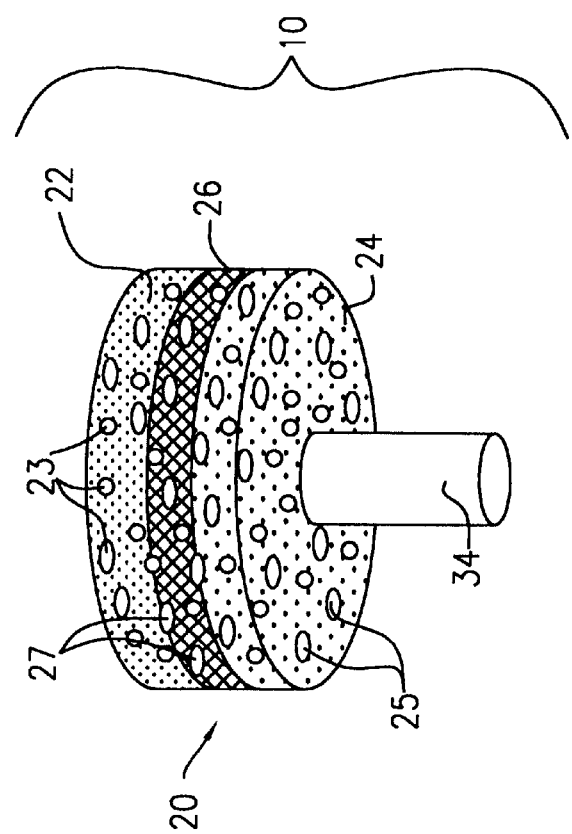
FIG. 2 is a bottom perspective view of the implant of FIG. 1.
Figure 1:
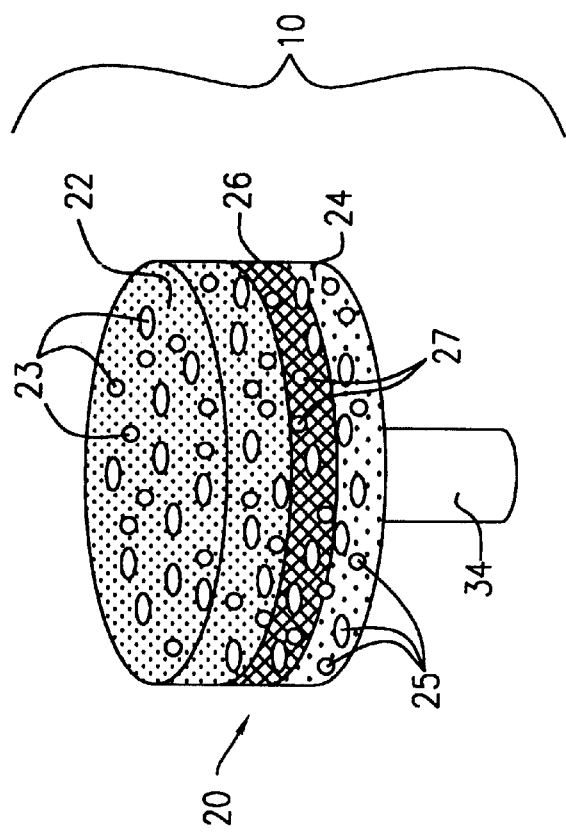
FIG. 1 is a top perspective view of an implant in accordance with an exemplary embodiment of the present invention.

This invention includes an implantable device with a scaffold component and a fixation component for mechanically holding the scaffold component in position relative to a tissue defect to be repaired. The scaffold component is formed around a scaffold support platform of the fixation component and has a porous biocompatible polymer layer attached to a porous ceramic layer via a porous transitional interface. The scaffolds are particularly useful in the repair/regeneration of defects present at a junction of tissue types exhibiting a transitional or gradient morphology/physiology such as at the cartilage/bone junction. The present invention can be utilized to repair/regenerate a tissue junction by inducing one cell type to proliferate in the polymer phase of the scaffold and a second cell type to grow in the ceramic phase of the scaffold. Examples of such junction regeneration sites are (a) spinal disc (nuclear and annular cells cultured on the polymer phase and osteoblasts cultured in the ceramic phase); (b) articular or meniscal cartilage (chondrocytes or fibrochondrocytes, respectively, cultured on the polymer phase and osteoblasts cultured in the ceramic). The present invention may also be utilized to repair the meniscus, fibrocartilage, tendons, and ligaments. The features of the porous polymer phase can be controlled to suit a desired application by choosing the appropriate conditions during the process of lyophilization, or freeze drying. The porous polymer foam can be directly lyophilized into the ceramic structure creating a multiphasic material composed of a polymer foam with or without reinforcement structures, an interphase zone of polymer foam diffused within and interlocking with the porous ceramic, and the is porous ceramic. A portion of the fixation component may be placed between the polymer and ceramic layers, which are structurally integrated to resist detachment of the scaffold component from the fixation component and/or delamination of the composite scaffold under in vivo conditions. The implant may be partially or completely absorbable.

The interphase zone exhibits a microporous polymer foam located within the macropores of a porous ceramic. The interpenetration of the two porous layers creates a strong mechanical junction while simultaneously providing a gradual change in material properties for the purpose of regenerating different tissues or co-culturing different types of cells in intimate contact with one another. The interconnecting pores and channels facilitate the transport of nutrients and/or invasion of cells into the scaffold, facilitating the ingrowth of tissue and more closely mimicking naturally occurring tissue junctions. The present invention therefore facilitates cellular organization and the regeneration of tissue junctions with normal morphology and physiology. The composition and features of the scaffold 20 are described in a copending Application filed contemporaneously herewith, entitled, "Porous Ceramic/Porous Polymer Layered Scaffolds for the Repair and Regeneration of Tissue, (Serial No. to be assigned) and assigned to the present assignee, such application being incorporated by reference herein.

The features of a scaffold in accordance with the present invention can be tailored to suit a particular application by selecting the appropriate ceramic, polymer and conditions for lyophilization of the polymer to obtain one or more of the following properties: (1) interconnecting polymer foams attached to the porous ceramic (2) a variety of porosities ranging from about 20% to about 98% for the polymer foam; (3) a gradient in the pore size between the polymer and ceramic; (4) channels that run through the porous polymer foam for improved cell invasion, vascularization and nutrient diffusion; and (5) micro-patterning of pores or the addition of other polymer structures on the surface of the polymer for cellular organization or to limit cellular invasion.

In addition, the scaffold can include (1) porous composites with a composition gradient to elicit or take advantage of different cell response to different materials; (2) reinforcement with knitted, braided, woven, or non-woven fabrics or meshes, or truss structures in order to impart desired mechanical properties; (3) blends of different polymer compositions to create a polymer phase that has portions that will break down at different rates; (4) multi-layer composite structures with layers of alternating porous ceramics and polymers; (5) a polymer phase co-lyophilized or coated with pharmaceutically active compounds; (6) a ceramic phase coated with pharmaceutically active compounds such as growth factors and/or (7) cells which may be cultured prior to or at the time of implantation.

Figure 3:
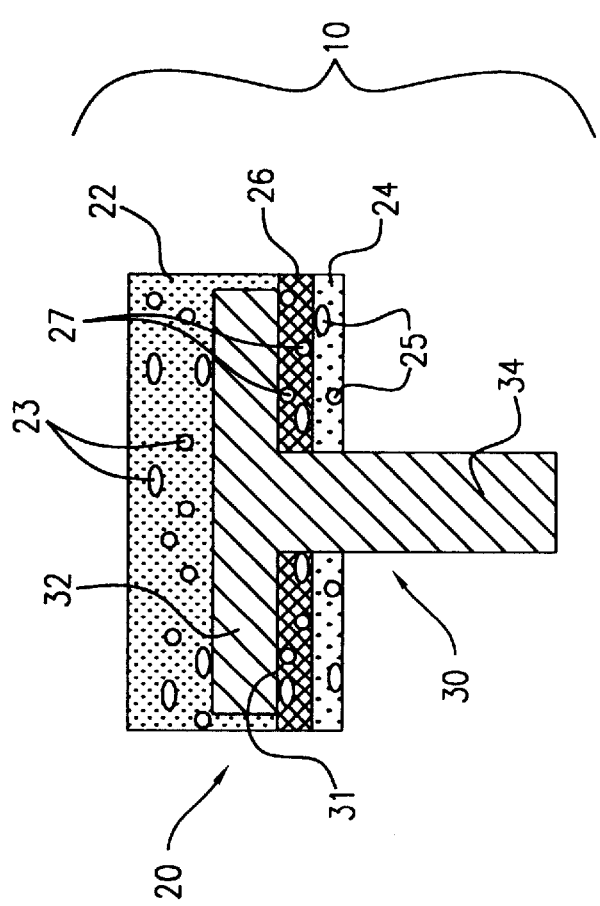
FIG. 3 is a cross-sectional view of the implant of FIGS. 1 and 2.

Referring to FIGS. 1 through 4, the implant 10 includes a scaffold component 20 and a fixation component 30 (See FIG. 3). Scaffold component 20 has polymeric phase 22 and ceramic phase 24, which are mechanically interlocked at interphase region 26. Polymeric phase 22, ceramic phase 24, and interphase region 26 preferably have pores 23, 25, 27, respectively, with an open cell structure. As shown in FIG. 3, fixation component 30 includes scaffold support 32 and anchoring post 34. Though not shown in the figures, anchoring post 34 may feature ribs, serrations, or other surface roughness or engagement features that improve the attachment of anchoring post 34 to the implant site, e.g., a hole in bone tissue. A preferred fixation component for use in the present invention is described in U.S. patent application Ser. No. 09/793,029, entitled, "Scaffold Fixation Device For Use In Articular Cartilage Repair", filed on Feb. 26, 2001, assigned to the present assignee and which is hereby incorporated herein by reference.

The implant 10 must have structural integrity to facilitate ease of handling in an operating room environment, i.e., scaffold component 20 and fixation component 30 must not separate before, during, or after the surgical procedure. Adequate strength and physical properties are developed in the implant through the selection of materials used to form the scaffold 20 and fixation 30 components, and the manufacturing process.

Figure 4:
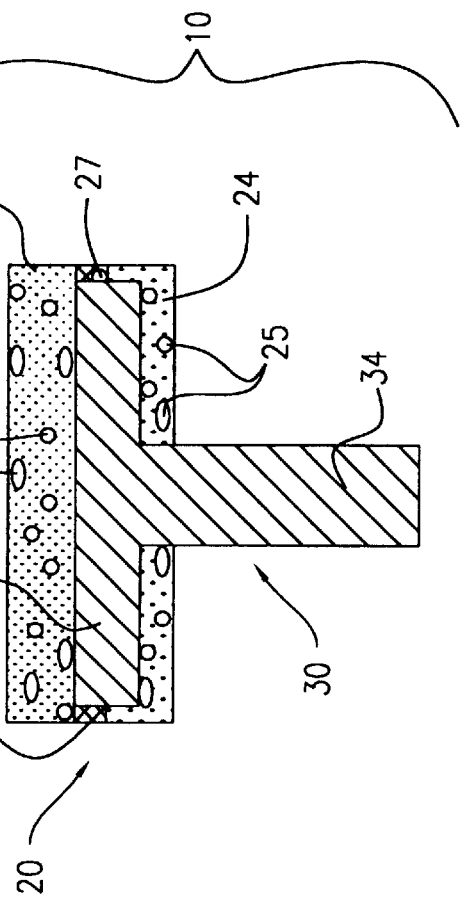
FIG. 4 is a cross-sectional view like FIG. 3 of an alternative embodiment of the present invention.

As shown in FIGS. 3 and 4, the scaffold component 20 fully encapsulates scaffold support 32 of the fixation component 30. This encapsulation serves as the means of attaching the scaffold component 20 to the fixation component 30. FIG. 3 shows scaffold support 32 of the fixation component 30 embedded in the polymeric phase 22 with the lower surface 31 abutting the interphase region 26. In a preferred embodiment shown in FIG. 4, scaffold support 32 of the fixation component 30 is fully encapsulated in all three components 22, 24, 26 of scaffold component 20. This is achieved by fully or partially countersinking scaffold support 32 in ceramic phase 24.

The infusion of the polymeric phase 22 into the ceramic phase 24 securely fastens the two phases 22, 24 and supports the brittle structure of the porous ceramic phase 24. The polymer 22 acts as a cushion to dissipate impact energy to shield the brittle ceramic 24 from catastrophically damaging stresses.

In addition, the communicating pores 23, 25, 27 encourage the growth of different types of cells, promoting the regeneration of different adjoining layers of tissue at an injured tissue junction.

The pores 25 in the ceramic phase 24 are interconnected, and may be selected to have pore sizes ranging from 25 to 600 microns, preferably from 100 to 250 microns. The pores 23 in the polymeric phase 22 are also interconnected and range in size from about 10 to 250 microns, preferably 30 to 150 microns. The terms "micropore" and "macropore" may be used to designate the two size scales of pores 23, 25 found in the scaffold 10. If the brittle ceramic phase 24 is cracked, the polymeric phase 22 in the interphase region 26 holds the scaffold component 20 together. The composite scaffold component 20 facilitates the creation of a strong bond between different types of tissue such as in the repair and regeneration of articular cartilage, meniscus, and spinal discs.

The embedding of fixation component 30 within the scaffold component 20 minimizes their combined thickness minimizing the depth of the hole in the tissue made to receive the implant 10 and the associated damage to the tissue proximate to the defect. In addition, ceramic phase 24 of scaffold component 20 (in conjunction with the polymeric phase 22) provides support to the hard tissue surrounding the implant, minimizing the likelihood of the collapse of hard tissue in the region of implant device 10, as well as facilitating the regeneration of mineralized hard tissue (bone).

The implant device 10 may be fabricated by feeding anchoring post 34 of fixation component 30 through a hole in ceramic phase 28 such that scaffold support 32 rests on top of, or in a countersunk region of, ceramic phase 24. This assembly is then partially introduced into a polymer-solvent system allowing the polymer-solvent system to infiltrate into the porous ceramic phase.

The polymer phase 22 is then foamed. The desired polymers may be foamed by lyophilization, supercritical solvent foaming (i.e., as described in EP 464163B1), gas injection extrusion, gas injection molding or casting with an extractable material (i.e., salts, sugar or any other means known to those skilled in the art). It should be appreciated that the scaffold support 32 may have openings therein through which the polymer 22 may contact the ceramic 14

It is preferred to foam the polymer 22 by lyophilization, or freeze drying. Suitable methods for lyophilizing elastomeric polymers to form foams is described in the following example and in the pending U.S. patent applications entitled, "Process for Manufacturing Biomedical Foams", Ser. No. 09/345,095, filed Jun. 30, 1999 and "Porous Tissue Scaffoldings for the Repair or Regeneration of Tissue", Ser. No. 09/345,096, filed Jun. 30, 1999, both assigned to Ethicon, Inc. and hereby incorporated herein by reference.

Figure 5:
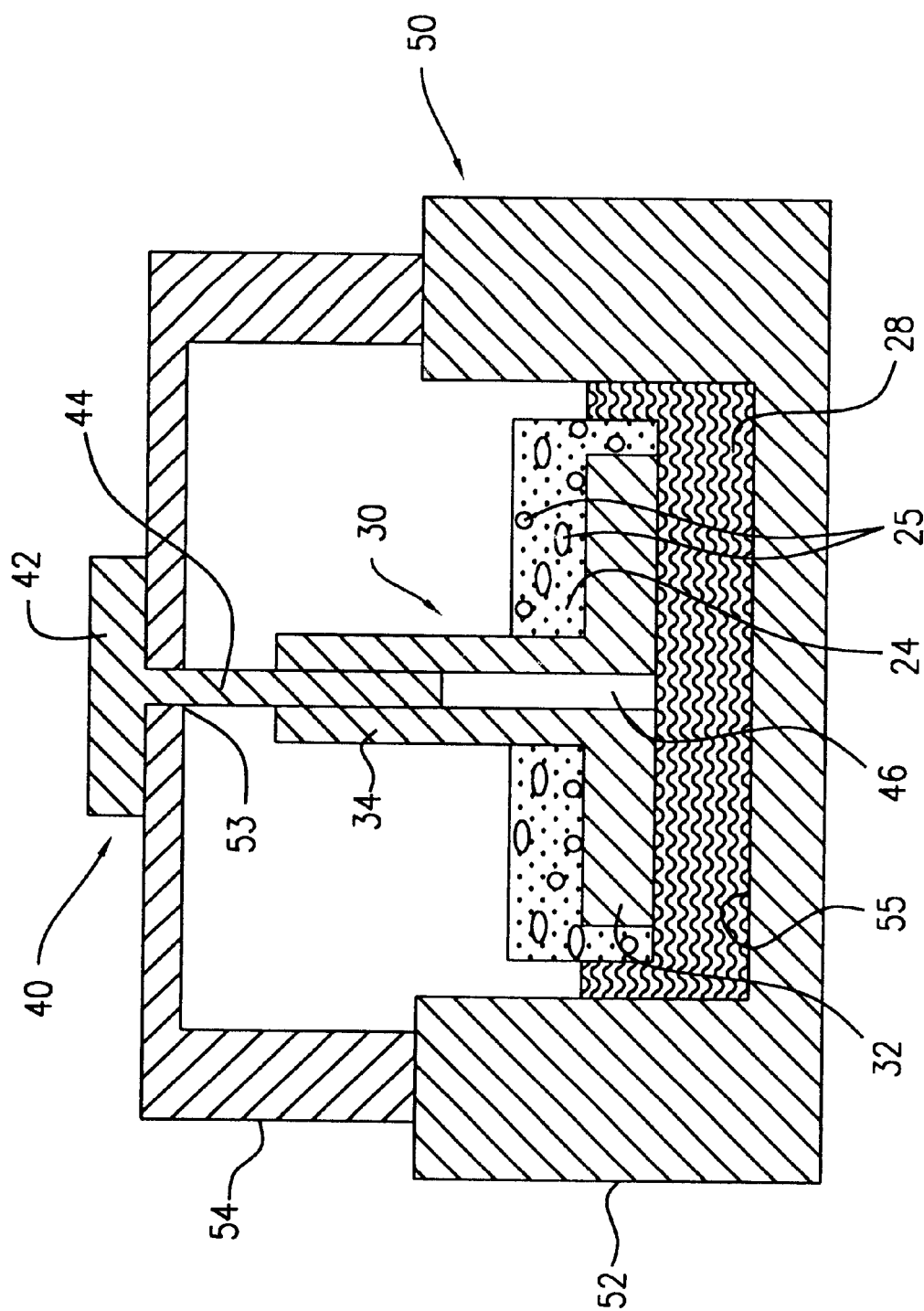
FIG. 5 is a diagrammatic cross-sectional view of the implant of FIG. 4 within a mold for fabricating the implant.

FIG. 5 illustrates a molding apparatus 50 having mold 52 and support bracket 54. Support bracket 54 includes a through hole 53 which is aligned over the well 55 of mold 52. A holder 40, having head 42 and pin 44, may be used to hold fixation component 30. Pin 44 passes through hole 53 with head 42 abutting support bracket 54. Pin 44 inserts into bore 46, holding fixation components 30 over the well 55 pendulously, by a friction fit.

Polymer-solvent system 28 is infused into the well 55 of mold 52, to a level such that polymer-solvent system 28 contacts ceramic phase 24. Polymer-solvent system 28 is of low viscosity and wicks via capillary action into ceramic phase pores 25. Other methods of infiltrating include, but are not limited to, injecting the polymer-solvent system into the ceramic 24 under pressure and vacuum assisted infiltration. The orientation of fixation component 30 within the polymer-solvent system 28 determines the orientation of the fixation component 30 within implant 10. Although the means of aligning fixation component 30 in the well 55 of mold 52 include support bracket 54 and a friction fit between connector pin 44 of holder 40 and fixation component 30, other means to accomplish the same objective should be readily apparent to one skilled in the art. The mold 52 can be made from any material that does not chemically react with the polymer-solvent system 28 and is preferably formed from a heat conductive material.

The molding apparatus 50 is placed in a lyophilizer (freeze dryer). to undergo directional cooling through the wall of mold 52 that is in contact with the lyophilizer shelf, which is subjected to a thermal cycle. The heat transfer front moves upwards from the lyophilizer shelf through the mold wall into the polymer-solvent system 28. When the temperature of the polymer solution goes below the gelation and/or freezing point, it separates into polymer and solvent phases giving rise to the cell/foam structure.

The pore morphology that results from the freezing step is a function of solution thermodynamics, freezing rate, temperature to which it is cooled, concentration of the solution, the presence of reinforcement elements, the presence of an adjoining layer, the occurrence of homogeneous or heterogeneous nucleation etc. Detailed descriptions of these phase separation phenomena are known in the art and can be found in the references "Microcellular foams via phase separation" by A. T. Young, *J. Vac. Sci. Technol.*, A 4(3), May/June 1986; and "Thermodynamics of Formation of Porous Polymeric Membrane from Solutions" by S. Matsuda, *Polymer J.* 23(5), (1991) 435. The lyophilization process can therefore be used to bond the polymer and ceramic layers 22, 24 while simultaneously creating a composite material with the correct pore structure to regenerate tissue.

The porous ceramic phase 24 of the scaffold may be composed of mono-, di-, tri-, α-tri, β-tri, and tetra-calcium phosphate, hydroxyapatite, fluoroapatites, calcium sulfates, calcium fluorides, calcium oxides, calcium carbonates, magnesium calcium phosphates, bioglasses, and mixtures thereof. There are a number of suitable porous biocompatible ceramic materials currently available on the commercial market such as Surgibone (Unilab Surgibone, Inc., Canada), Endobon (Merck Biomaterial France, France), Ceros (Mathys, A. G., Bettlach, Switzerland), and Interpore (Interpore, Irvine, Calif., U.S.).

Alternatively, the ceramic phase 14 may be in the form of a porous polymer matrix with inclusions of short ceramic fibers or particulates. This alternative ceramic phase 14 may be formed by conventional methods for working plastics, such as injection molding, with the porosity thereof provided by leachable inclusions, molds with pore forming pins, or drilling.

The polymeric phase 22 may be either a natural or synthetic polymer, or combinations of both. Natural biopolymers include collagen, elastin, alginate, chitin, hyaluronic acid, and others. Examples of suitable synthetic biocompatible, bioabsorbable polymers that could be used include aliphatic polyesters, poly(amino acids), copoly (ether-esters), polyalkylene oxalates, polyamides, poly (iminocarbonates), polyorthoesters, polyoxaesters, polyamidoesters, polyoxaesters containing amine groups, poly(anhydrides), polyphosphazenes, biomolecules and blends thereof.

For the purpose of this invention aliphatic polyesters include but are not limited to homopolymers and copolymers of lactide (which includes lactic acid, D-, L- and meso lactide), glycolide (including glycolic acid), ε-caprolactone, p-dioxanone (1,4-dioxan-2-one), trimethylene carbonate (1,3-dioxan-2-one), alkyl derivatives of trimethylene carbonate, δ-valerolactone, β-butyrolactone, γ-butyrolactone, γ-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one, 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one and polymer blends thereof.

Poly(iminocarbonates) for the purpose of this invention include those described by Kemnitzer and Kohn, in the *Handbook of Biodegradable Polymers*, edited by Domb, Kost and Wisemen, Hardwood Academic Press, 1997, pages 251–272. Copoly(ether-esters) for the purpose of this invention include those copolyester-ethers described by Cohn and Younes *J. Biomater. Res.*, 22, (1988) 993, and Cohn, *Polymer Preprints*, 30(1), (1989) 498.

Polyalkylene oxalates for the purpose of this invention include those described in U.S. Pat. Nos. 4,208,511; 4,141,087; 4,130,639; 4,140,678; 4,105,034; and 4,205,399 (incorporated by reference herein).

Polyphosphazenes for the purpose of this invention include co-, ter- and higher order mixed monomer based polymers made from L-lactide, D,L-lactide, lactic acid, glycolide, glycolic acid, para-dioxanone, trimethylene carbonate and ε-caprolactone those described by Allcock in *The Encyclopedia of Polymer Science*, Wiley Intersciences, John Wiley & Sons, 13 (1988) 31, and by Vandorpe, Schacht, Dejardin and Lemmouchi in the *Handbook of Biodegradable Polymers*, edited by Domb, Kost and Wisemen, Hardwood Academic Press, (1997) 161 (which are hereby incorporated by reference herein).

Polyanhydrides for the purpose of this invention include those from diacids of the form HOOC—$C_6H_4$—O—$(CH_2)_m$—O—$C_6H_4$—COOH where m is an integer in the range of from 2 to 8 and copolymers thereof with aliphatic alpha-omega diacids of up to 12 carbons.

Polyoxaesters, polyoxaamides and polyoxaesters containing amines and/or amino groups for the purpose of this invention include those described in one or more of the following U.S. Pat. Nos. 5,464,929; 5,595,751; 5,597,579; 5,607,687; 5,618,552; 5,620,698; 5,645,850; 5,648,088; 5,698,213; 5,700,583; and 5,859,150 (which are incorporated herein by reference). Polyorthoesters for the purpose of this invention include those described by Heller in the *Handbook of Biodegradable Polymers*, edited by Domb, Kost and Wisemen, Hardwood Academic Press, (1997), 99 (hereby incorporated herein by reference).

Aliphatic polyesters are preferred for making the polymer phase 22. Aliphatic polyesters can be homopolymers, copolymers (random, block, segmented, tapered blocks, graft, triblock, etc.) having a linear, branched or star structure. The preferred morphology of the copolymer chains is linear. Suitable monomers for making aliphatic homopolymers and copolymers may be selected from the group consisting of, but not limited to, lactic acid, lactide (including L-, D-, meso and D,L mixtures), glycolic acid, glycolide, ε-caprolactone, p-dioxanone (1,4-dioxan-2-one), trimethylene carbonate (1,3-dioxan-2-one), delta-valerolactone, beta-butyrolactone, epsilon-decalactone, 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 6,6-dimethyl-dioxepan-2-one, 6,8-dioxabicycloctane-7-one and combinations thereof.

Elastomeric copolymers also are particularly useful in the present invention. Suitable bioabsorbable, biocompatible elastomers include, but are not limited to, those selected from the group consisting of elastomeric copolymers of ε-caprolactone and glycolide (preferably having a mole ratio of ε-caprolactone to glycolide of from about 35:65 to about 65:35, more preferably from 45:55 to 35:65); elastomeric copolymers of ε-caprolactone and lactide, including L-lactide, D-lactide blends thereof or lactic acid copolymers (preferably having a mole ratio of ε-caprolactone to lactide of from about 35:65 to about 65:35 and more preferably from 45:55 to 30:70 or from about 95:5 to about 85:15); elastomeric copolymers of p-dioxanone (1,4-dioxan-2-one) and lactide including L-lactide, D-lactide and lactic acid (preferably having a mole ratio of p-dioxanone to lactide of from about 40:60 to about 60:40); elastomeric copolymers of ε-caprolactone and p-dioxanone (preferably having a mole ratio of ε-caprolactone to p-dioxanone of from about 30:70 to about 70:30); elastomeric copolymers of p-dioxanone and trimethylene carbonate (preferably having a mole ratio of p-dioxanone to trimethylene carbonate of from about 30:70 to about 70:30); elastomeric copolymers of trimethylene carbonate and glycolide (preferably having a mole ratio of trimethylene carbonate to glycolide of from about 30:70 to about 70:30); elastomeric copolymer of trimethylene carbonate and lactide including L-lactide, D-lactide, blends thereof or lactic acid copolymers (preferably having a mole ratio of trimethylene carbonate to lactide of from about 30:70 to about 70:30); and blends thereof. Examples of suitable bioabsorbable elastomers are also described in U.S. Pat. Nos. 4,045,418, 4,057,537 and 5,468,253, all hereby incorporated by reference.

In the preferred embodiments of this invention, the elastomer from which the foams are formed will exhibit a percent elongation greater than about 200 percent and preferably greater than about 500 percent. The properties that determine the degree of elasticity of the bioabsorbable elastomer are achieved while maintaining a tensile strength greater than about 500 psi, preferably greater than about 1,000 psi, and a tear strength of greater than about 50 lbs/inch, preferably greater than about 80 lbs/inch.

The polymer or copolymer suitable for forming the polymer phase 22 for any particular application depends on several factors. The chemical composition, spatial distribution of the phases, the molecular weight of the polymer and the degree of crystallinity, all dictate to some extent the in vitro and in vivo behavior of the polymer. However, the selection of the polymer to make foams for tissue regeneration largely depends on (but is not limited to) the following factors: (a) bioabsorption (or biodegradation) kinetics; (b) in vivo mechanical performance; (c) cell response to the material in terms of cell attachment, proliferation, migration and differentiation and (d) biocompatibility.

The ability of the polymer phase to resorb in a timely fashion in vivo is critical. The differences in the absorption time under in vivo conditions can also be the basis for combining two different copolymers. For example, a copolymer of 35:65 ε-caprolactone and glycolide (a relatively fast absorbing polymer) is blended with 40:60 ε-caprolactone and (L)lactide copolymer (a relatively slow absorbing polymer) to form a foam. Such a foam could be processed to yield several different physical structures depending upon the technique used. The two phases can be either randomly inter-connected bicontinuous phases, or have a gradient or laminate composition with an integrated interface between the phase layers. The microstructure of these foams can be optimized to regenerate or repair the desired anatomical features of the tissue that is being engineered.

Suitable solvents for the preferred absorbable aliphatic polyesters that will not affect the ceramic foams include but are not limited to solvents selected from a group consisting of formic acid, ethyl formate, acetic acid, hexafluoroisopropanol (HFIP), cyclic ethers (i.e. THF, DMF, and PDO), acetone, acetates of C2 to C5 alcohol (such as ethyl acetate and t-butylacetate), glyme (i.e. monoglyme, ethyl glyme, diglyme, ethyl diglyme, triglyme, butyl diglyme and tetraglyme) methylethyl ketone, dipropyleneglycol methyl ether, lactones (such as γ-valerolactone, δ-valerolactone, β-butyrolactone, γ-butyrolactone) 1,4-dioxane, 1,3-dioxolane, 1,3-dioxolane-2-one (ethylene carbonate), dimethlycarbonate, diethylcarbonate, benzene, toluene, benzyl alcohol, p-xylene, naphthalene, tetrahydrofuran, N-methyl pyrrolidone, dimethylformamide, chloroform, 1,2-dichloromethane, morpholine, dimethylsulfoxide, hexafluoroacetone sesquihydrate (HFAS), anisole and mixtures thereof. Among these solvents, the preferred solvent is 1,4-dioxane. A homogeneous solution of the polymer in the solvent is prepared using standard techniques.

Additionally, polymer-solvent system 28 can be solidified with various reinforcements such as films, scrims, woven, nonwoven, knitted or braided textile structures incorporated therein. In addition to altering the mechanical properties of the polymer 22, reinforcements can be utilized: (i) to modify the in vitro behavior of the polymer 22, e.g., by introducing a different in vitro profile; (ii) as a carrier for the controlled release of a drug; and (iii) as a carrier for Micro-Electro Mechanical Systems (MEMS).

Solids may be added to the polymer-solvent system 28 during the processing of the implant 10 to act as buffers, reinforcing materials, porosity modifiers, and/or radioopaque markers to allow imaging after implantation. Suitable solids include, but are not limited to, particles of demineralized bone, calcium phosphate particles, calcium carbonate particles for bone repair, leachable solids for pore creation and particles of bioabsorbable polymers not soluble in the solvent system as reinforcing agents or for the creation of pores as they are absorbed.

Suitable leachable solids include but are not limited to nontoxic leachable materials such as salts (i.e., sodium chloride, potassium chloride, calcium chloride, sodium tartrate, sodium citrate, and the like) biocompatible mono and disaccharides (i.e., glucose, fructose, dextrose, maltose, lactose and sucrose), polysaccharides (i.e., starch, alginate), water soluble proteins (i.e., gelatin and agarose) and paraffin. Generally all of these materials will have an average diameter of less than about 1 mm and preferably will have an average diameter of from about 50 to about 500 μm. The particles will generally constitute from about 1 to about 50 volume percent of the total volume of the particle and polymer-solvent mixture (wherein the total volume percent equals 100 volume percent). The leachable materials can be removed by immersing the foam with the leachable material in a solvent in which the particle is soluble for a sufficient amount of time to allow leaching of substantially all of the particles, but which does not dissolve or detrimentally alter the foam. The preferred extraction solvent is water, most preferably distilled-deionized water. This process is described in U.S. Pat. No. 5,514,378, hereby incorporated herein by reference. Preferably the foam will be dried after the leaching process is complete at low temperature and/or vacuum dried to minimize hydrolysis of the foam unless accelerated absorption of the foam is desired.

Various proteins (including short chain peptides), growth agents, chemotatic agents and therapeutic agents (antibiotics, analgesics, anti-inflammatories, anti-rejection (e.g. immunosuppressants) and anticancer drugs), or ceramic particles can be added to the composite scaffold 20 during processing or adsorbed onto the surface or back-filled into the scaffold 20 after fabrication. The pores 25 of the ceramic phase 24 and/or the pores 23 of the polymer 22 may be partially or completely filled with biocompatible resorbable synthetic polymers or polymers (such as collagen or elastin) or biocompatible ceramic materials (such as hydroxyapatite) and combinations thereof (that may or may not contain materials that promote tissue growth). Suitable materials include but are not limited to autograft, allograft, or xenograft bone, bone marrow, morphogenic proteins (BMPs), epidermal growth factor (EGF), fibroblast growth factor (FGF), platelet derived growth factor (PDGF), insulin derived growth factor (IGF-I and IGF-II), transforming growth factors (TGF-β), vascular endothelial growth factor (VEGF), platelet rich plasma (PRP) or other osteoinductive or osteoconductive materials known in the art. The polymer fillers could also be conductive or chemotactic materials, or delivery vehicles for growth factors. Examples would be recombinant or animal derived collagen or elastin or hyaluronic acid.

Bioactive coatings or surface treatments could also be applied to the surface of the implant 10. For example, bioactive peptide sequences (RGDs) could be applied to facilitate protein adsorption and subsequent cell tissue attachment.

Therapeutic agents may also be delivered via the implant 10. The polymers and blends that are used to form the scaffold 20 can contain therapeutic agents. For example, polymer 22 would be mixed with a therapeutic agent prior to forming the composite scaffold 20 or loaded into the scaffold after it is formed. The variety of different therapeutic agents that can be used in conjunction with the implant 10 of the present invention is vast. In general, therapeutic agents which may be administered via the implant 10 include, without limitation: anti-infectives such as antibiotics and antiviral agents; chemotherapeutic agents (i.e. anticancer agents); anti-rejection agents; analgesics and analgesic combinations; anti-inflammatory agents; hormones such as steroids; growth factors (bone morphogenic proteins (i.e. BMPs 1–7), bone morphogenic-like proteins (i.e. GFD-5, GFD-7 and GFD-8), epidermal growth factor (EGF), fibroblast growth factor (i.e. FGF 1–9), platelet derived growth factor (PDGF), insulin like growth factor (IGF-I and IGF-II), transforming growth factors (i.e. TGF-βI-III), vascular endothelial growth factor (VEGF)); and other naturally derived or genetically engineered proteins, polysaccharides, glycoproteins, or lipoproteins. These growth factors are described in *The Cellular and Molecular Basis of Bone Formation and Repair* by Vicki Rosen and R. Scott Thies, published by R. G. Landes Company hereby incorporated herein by reference.

Composite scaffolds 20 containing bioactive materials may be formulated by mixing one or more therapeutic agents with the polymer used to make the polymer phase 22, with the solvent, or with the polymer-solvent mixture that is then foamed via lyophilization. Alternatively, a therapeutic agent may be coated on the composite scaffold 20 with a pharmaceutically acceptable carrier that does not dissolve the scaffold 20. The therapeutic agents, may be a liquid, a finely divided solid, or any other appropriate physical form. Typically, but optionally, the matrix will include one or more additives, such as diluents, carriers, excipients, stabilizers or the like. The type of polymer and drug concentration can be varied to control the release profile and the amount of drug dispensed. Upon contact with body fluids, the drug will be released. If the drug is incorporated into the scaffold 20, then the drug is released as it undergoes gradual degradation (mainly through hydrolysis). This can result in prolonged delivery (over, say 1 to 5,000 hours, preferably 2 to 800 hours) of effective amounts (say, 0.0001 mg/kg/hour to 10 mg/kg/hour) of the drug.

As outlined in Vacanti, U.S. Pat. No. 5,770,417, cells can be harvested from a patient (before or during surgery to repair the tissue) and the cells can be processed under sterile conditions to provide a specific cell type (i.e., pluripotent cells, stem cells, marrow cells, progenitor human autologous adipose tissue (PHAAT) cells or precursor cells, such as, the mesenchymal stem cells described in Caplan, U.S. Pat. No. 5,486,359). These cells, e.g., myocytes, adipocytes, fibromyoblasts, ectodermal cell, muscle cells, osteoblast (i.e. bone cells), chondrocyte (i.e. cartilage cells), endothelial cells, fibroblast, pancreatic cells, hepatocyte, bile duct cells, bone marrow cells, neural cells, genitourinary cells (including nephritic cells) and combinations thereof may be applied or seeded into the porous composite scaffold 20. Autogenous, allogeneic, xenogeneic cells may be used. The cells may be cultured ex vivo and then reimplanted. Tissue may be harvested from a patient, processed to select certain cells and/or growth factors, such as PRP (platelet rich plasma), and then reimplanted with the implant 10 back into the patient. The implanted cells could also contain inserted DNA encoding a protein that could stimulate the attachment, proliferation or differentiation of tissue.

Cells may be implanted into the scaffold 20 by placing the scaffold 20 in a cell culture such that the cells invade the micropores 23 and macropores 25. The scaffold 20 can then be implanted into the patient. The in vitro seeding of cells could provide for a more rapid development and differentiation process for the tissue. It is clear that cellular differentiation and the creation of tissue specific extracellular matrix is critical for the tissue engineering of a functional implant. It is known that different cell types (stromal cells and chondrocytes) can be cultured on different structures. A gradient structure also allows for co-cultured tissue scaffolds 20 to be generated.

One use of the construct described herein is for the repair and regeneration of articular cartilage. Articular cartilage is an example of a naturally occurring structure composed of four different zones that include the superficial or tangential zone within the first 10–20% of the structure (this includes the articular surface), the middle zone, which is 40–60% of the middle structure, the deep zone that is adjacent to the tide mark, and a transition zone between the bone and cartilage that is composed of calcified cartilage. Subchondral bone is located adjacent to the tide mark and this transitions into cancellous bone. As described above, the present invention permits the fabrication of a scaffold, e.g., 20 having multiple layers, each having its own characteristics of composition, porosity, strength, etc. Accordingly, the scaffold, e.g., 20 may act as a template for multiple distinct tissue zones as are present in articular cartilage.

The surface porosity of the polymer phase 22 can be controlled by various methods including providing a mold 52 therefore having a plurality of upstanding pins for piercing the surface during molding or subsequently piercing the surface by needles, laser treatment, chemical treatment, etc., resulting in surface porosity ranging from impervious to porous, and thereby determining fluid permeability. With regard to fabricating a scaffold 20 for repairing articular cartilage, the scaffold 20 may have three zones, viz., a porous polymeric phase 22 which lies adjacent to cartilage tissue, a porous ceramic phase 24 which lies adjacent to bone tissue, and an interphase region 26. The polymer phase 22 would have an upper surface (skin), which may be provided with a porosity, e.g., 75 to 150 $\mu$m to enable the passage of cells to promote in growth. For articular cartilage, the polymer phase 22 and ceramic phase 24 in conjunction with the fixation component 30, will need to support mechanical loading and thereby protect the invading cells until they have differentiated and consolidated into tissue that is capable of supporting a load. The polymer phase 22 may have a porosity of about 80 to about 95 percent with pores that are of the order of 100 $\mu$m (about 80 $\mu$m to about 120 $\mu$m). It is expected that chondrocytes will invade this zone. The ceramic phase 24 may have larger pores (about 250 $\mu$m to about 400 $\mu$m) and a porosity in the range of about 50 to about 95 percent which is structurally compatible with cancellous bone. The interphase region 26 resembles the structural transition between cartilage and bone.

Several patents have proposed systems for repairing cartilage that could be used with porous scaffolds of the present invention. For example, U.S. Pat. No. 5,769,899 describes a device for repairing cartilage defects and U.S. Pat. No. 5,713,374, describes securing cartilage repair devices with bone anchors (both hereby incorporated herein by reference)

The implant 10 described herein may be used for meniscal repair and regeneration, exhibiting biocompatibility, resistance to crumbling at the time of surgery, sufficient resistance to compression to allow cell invasion under load, and high porosity. The implant is easily sterilized, remodeled by invading tissue, and degrades as new tissue is being formed. Furthermore, the scaffold component 20 may be securely fixed to the site of injury via the fixation component 30.

The implant 10 may have bi-, tri-, or multi-layered scaffolds 20. These layers may be spaced at regular or irregular intervals and the polymeric phases may be reinforced with a number of reinforcements, with the fixation component 30 residing at any desired level within the scaffold 20. The reinforcements may be in fabric, truss, or particulate form and may be placed at different heights, angles, conformations or gradients in the foam. Both the polymer 22 and ceramic 24 phases may have different porosities depending on the application and may have open cell or closed cell structures.

The implant 10 may be affixed to the tissue to be repaired by inserting the post 34 into a suitably sized hole in the tissue, e.g., bone. A fixative such as calcium phosphate or calcium sulfate cements, PMMA, fibrin glue, adhesives (i.e. cyanoacrylates, butyl acrylates, etc.) may also be used to secure the implant 10.

The following example is illustrative of the principles and practice of this invention, although not limited thereto. Numerous additional embodiments within the scope and spirit of the invention will become apparent to those skilled in the art.

In the following example, the abbreviation PCL indicates polymerized ε-caprolactone, PGA indicates polymerized glycolide, and PLA indicates polymerized (L)lactide. Additionally, the percentage in front of the copolymer indicates the respective mole percentage of each phase.

EXAMPLE 1

This example describes the preparation of a composite scaffold with an integral fixation device.

A solution of the polymer to be lyophilized into a foam was prepared, composed of a 95/5 weight ratio of 1,4-dioxane to 35/65 PCL/PGA. The polymer and solvent were placed into a flask which was placed into a water bath and heated to 70° C. The solution was heated and stirred for 5 hours. Afterwards, the solution was filtered using an extraction thimble (extra coarse porosity, type ASTM 170–220 (EC)) and stored in the flask.

A ceramic tablet of porous hydroxyapatite (CERAbio, Prescott, Wis.) was fabricated with the following dimensions: 7-mm outer diameter, 2 mm inner diameter and 2 mm thickness.

A bioabsorbable fixation component was manufactured using an injection molding process. The design of the fixation component used is described in copending U.S. patent application Ser. No. 09/793,029 entitled, "Scaffold Fixation Device For Use In Articular Cartilage Repair", which is incorporated herein by reference. The polymer used to manufacture the fixation components was a copolymer of 85% PLA and 15% PGA (85/15 PLA/PGA) produced by Purac (Gorinchem, The Netherlands) with an I.V. of 1.79 dL/g as measured in chloroform. The injection molder (Niigata NN35MI) had a barrel diameter of 18 mm. The hopper was fitted with a nitrogen purge to keep the polymer dry. The feed, transition and compression zone temperatures were 185° C., 185° C. and 191° C., respectively. The die and mold temperatures were 191° C. and 24° C., respectively. The maximum injection speed was 80 mm/s. Under cylinder number two, the maximum injection pressure was 85 Kgf/cm². The hold pressure was 70 Kgf/cm². The total time for injection and hold was 3 seconds and the cooling time at the end of hold cycle was 20 seconds.

The fixation component proposed by the foregoing process was threaded through the 2 mm hole prefabricated in the ceramic tablet and suspended approximately 1.0–1.5 millimeters above the bottom surface of a mold as described in reference to FIG. 5.

The previously prepared polymer solution was poured into the mold until it was filled. The scaffold support of the fixation device and the face of the ceramic disk contacting the scaffold support were submerged in the polymer solution with at least half the thickness of the ceramic disk submerged.

A laboratory scale lyophilizer (Model Freeze Mobile G from Virtis Company (Gardiner, N.Y.), was used in this example. The mold assembly was placed on the shelf of the lyophilizer (or freeze dryer) and the freeze dry sequence was executed. The freeze dry sequence used in this example was: 1) 20° C. for 15 minutes, 2) –5° C. for 180 minutes, 3) –5° C. for 180 minutes under vacuum 100 mT, 4) 5° C. for 120 minutes under vacuum 100 mT, and 5) 20° C. for 120 minutes under vacuum 100 mT. As the solution in the mold freeze dried, the polymeric phase receded, leaving an interphase region of less than 200 microns of polymeric foam infiltrating the porous ceramic. The scaffold support of the fixation device was embedded within the polymeric phase which was securely affixed to the ceramic phase.

What is claimed is:

1. A prosthetic implant, comprising:
   a composite tissue scaffold having a ceramic layer with a first plurality of pores and a polymer layer with a second plurality of pores, said polymer attached to said ceramic at an interphase region, said polymer infused at least partially into said first plurality of pores in said interphase region at least one of said polymer layer and said ceramic layer being biodegradable; and
   a fixation device with a scaffold support and an anchoring post, said anchoring post extending from a surface of said scaffold support at a selected angle, said anchoring post insertable into a receptacle formed in tissue, said scaffold support embedded within said scaffold.

2. The implant of claim 1, wherein a portion of said second plurality of pores communicate at least partially with said first plurality of pores in said interphase region.

3. The implant of claim 2, wherein said ceramic has a hole therein, said anchoring post extending through said hole, said scaffold support abutting against said ceramic proximate said hole, said scaffold support being larger than said hole, preventing said scaffold support from passing through said hole, said interphase region extending proximate to a periphery of said scaffold support.

4. The implant of claim 3, wherein said ceramic has a countersunk area disposed about said hole, said scaffold support being at least partially contained within said countersunk area.

5. The implant of claim 4, wherein said scaffold support has at least one opening extending therethrough, said at least one opening permitting said polymer to extend therethrough.

6. The implant of claim 1, further including a mechanical reinforcement embedded in said polymer, said mechanical reinforcement selected from the group consisting of films, scrims, woven textiles, non-woven textiles, knitted textiles, braided textiles and trusses.

7. The implant of claim 1, further including fillers within said polymer selected from the group consisting of growth factors and therapeutic materials.

8. The implant of claim 1, further including living cells residing on a surface of said scaffold.

9. The implant of claim 1, wherein said ceramic is selected from the group consisting of hydroxyapatite, tricalcium phosphate, tetracalcium phosphate, fluoroapatite, magnesium calcium phosphate, calcium sulfate, calcium fluoride, calcium oxide and calcium carbonate.

10. The implant of claim 1, wherein said polymer is selected from the group consisting of collagen, elastin, hyaluronic acid, chitin and alginate.

11. The implant of claim 1, wherein said polymer is selected from the group consisting of aliphatic polyester homopolymers and aliphatic polyester copolymers.

12. The implant of claim 11, wherein said polymer is selected from the group consisting of lactic acid, lactide mixtures of L-, D-, meso and D,L lactides, glycolic acid, glycolide, epsilon-caprolactone, p-dioxanone (1,4-dioxan-2-one) and trimethylene carbonate (1,3-dioxan-2-one).

13. The implant of claim 1, wherein said polymer is an aliphatic polyester elastomeric copolymer.

14. The implant of claim 13, wherein said copolymer is formed from epsilon-caprolactone and glycolide in a mole ratio of from about 35:65 to about 65:35.

15. The implant of claim 13, wherein said copolymer is formed from epsilon-caprolactone and glycolide in a mole ratio of from about 45:55 to about 35:65.

16. The implant of claim 13, wherein said copolymer is formed from epsilon-caprolactone and lactide selected from the group consisting of L-lactide, D-lactide and lactic acid copolymers in a mole ratio of epsilon-caprolactone to lactide of from about 35:65 to about 65:35.

17. The implant of claim 13, wherein said copolymer is formed from epsilon-caprolactone and lactide selected from the group consisting of L-lactide, D-lactide and lactic acid copolymers in a mole ratio of epsilon-caprolactone to lactide of from about 45:55 to about 30:70.

18. The implant of claim 13, wherein said copolymer is formed from epsilon-caprolactone and lactide selected from the group consisting of L-lactide, D-lactide and lactic acid copolymers in a mole ratio of epsilon-caprolactone to lactide of from about 95:5 to about 85:15.

19. A method for making a prosthetic implant having a tissue scaffold and an embedded fixation device with a scaffold support and an anchoring post, comprising the steps of:
  a) providing a porous ceramic body with a first set of pores and a hole extending therethrough;
  b) providing a polymer solution;
  c) inserting the anchoring post of the fixation device through the hole in the ceramic body such that the scaffold support contacts the ceramic body forming a first subassembly;
  d) placing the support scaffold and the ceramic body of the subassembly in contact with the polymer solution;
  e) permitting the polymer solution to at least partially infuse into pores in the ceramic body; and
  f) foaming the polymer solution to produce a polymer foam with a second set of pores, the polymer foam interlocking with the ceramic body where the polymer solution was permitted to infuse into the ceramic body and embedding the scaffold support within the resulting conjoined composite, with at least a portion of the first set of pores communicating with at least a portion of the second set of pores.

20. The method of claim 19, wherein said step of foaming is by lyophilization.

21. The method of claim 20, wherein said polymer solution is poured into a mold with a hollow well and an implant support overarching the well, and further comprising the step of suspending the implant from the implant support such that the subassembly is submerged in the polymer solution to a selected level.

22. The implant of claim 1, wherein said scaffold support has a generally flat first surface and a second surface substantially parallel to said first surface, said anchoring post extending from said second surface, said ceramic layer being juxtaposed next to said polymer layer with said scaffold support captured therebetween, said ceramic layer being disposed proximate said second surface and said polymer layer disposed proximate said first surface.

23. The implant of claim 22, wherein at least one of said ceramic layer and said polymer layer has a hollow therein for at least partially receiving said scaffold support.

24. The implant of claim 22, wherein said ceramic layer and said polymer layer each have a hollow therein for at least partially receiving said scaffold support.

* * * * *